US008134571B2

(12) United States Patent
Krishnan et al.

(10) Patent No.: US 8,134,571 B2
(45) Date of Patent: Mar. 13, 2012

(54) AUTOMATIC CAD ALGORITHM SELECTION

(75) Inventors: Arun Krishnan, Exton, PA (US); Jonathan Stoeckel, Hierden (NL)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1528 days.

(21) Appl. No.: 11/543,416

(22) Filed: Oct. 5, 2006

(65) Prior Publication Data
US 2007/0076934 A1 Apr. 5, 2007

Related U.S. Application Data

(60) Provisional application No. 60/723,873, filed on Oct. 5, 2005.

(51) Int. Cl.
*G06F 15/00* (2006.01)
*G06F 7/00* (2006.01)
*G09G 5/00* (2006.01)
*G06K 9/00* (2006.01)
*G06K 9/40* (2006.01)
*G06K 9/36* (2006.01)
*G06K 9/60* (2006.01)

(52) U.S. Cl. ........ 345/581; 345/501; 345/619; 382/128; 382/254; 382/276; 382/305; 707/705

(58) Field of Classification Search .................. 345/418, 345/581, 612, 501, 520, 619; 382/128, 254, 382/274, 276, 305; 600/300; 707/608, 661, 707/705, 758
See application file for complete search history.

(56) References Cited

U.S. PATENT DOCUMENTS

| 5,991,758 | A  | * | 11/1999 | Ellard .................................. 1/1 |
| 6,029,160 | A  | * | 2/2000  | Cabrera et al. ........................ 1/1 |
| 6,038,563 | A  | * | 3/2000  | Bapat et al. .......................... 1/1 |
| 7,558,413 | B2 | * | 7/2009  | Tu et al. ........................ 382/128 |
| 2002/0010679 | A1 | * | 1/2002 | Felsher ............................ 705/51 |
| 2006/0274928 | A1 | * | 12/2006 | Collins et al. ................. 382/132 |
| 2006/0291708 | A1 | * | 12/2006 | Dehmeshki et al. .......... 382/128 |
| 2009/0238540 | A1 | * | 9/2009  | Wright et al. .................... 386/95 |
| 2010/0029509 | A1 | * | 2/2010  | Huang et al. .................... 506/16 |
| 2010/0241595 | A1 | * | 9/2010  | Felsher .......................... 705/400 |

FOREIGN PATENT DOCUMENTS

| EP | 0 487 110 A2 | 5/1992 |
| WO | WO 2004/012145 A2 | 2/2004 |
| WO | WO 2005/017806 A | 2/2005 |

* cited by examiner

*Primary Examiner* — Wesner Sajous
(74) *Attorney, Agent, or Firm* — Peter Robert Withstandley

(57) ABSTRACT

A computer system for automatic selection of a computer-aided detection (CAD) algorithm including a database storing image data, a browser for navigating the data and selecting image data, an application receiving image data selected by the browser, and a selector selecting a CAD algorithm for processing the image data according to at least one of fixed attributes of the image data and an indication of a subject of the image data.

14 Claims, 3 Drawing Sheets

AUTOMATIC CAD ALGORITHM SELECTION

This application claims the benefit of Provisional Application No. 60/723,873 filed on Oct. 5, 2005 in the United States Patent and Trademark Office, the contents of which are herein incorporated by reference in its entirety.

BACKGROUND OF THE INVENTION

1. Field of the Invention

The present disclosure relates to computer-aided detection/diagnosis (CAD), and more particularly to a system and method for automatic CAD algorithm selection.

2. Description of Related Art

Many different CAD algorithms are available, for example, for the detection of lung nodules, detection of pulmonary emboli and detection of polyps in the colon. In clinical practice often no explicit knowledge about the body parts being imaged is available digitally. Thus, manual interaction is needed to select a CAD algorithm for processes the images.

Therefore, a need exists for a system and method of automatic CAD algorithm selection.

SUMMARY OF THE INVENTION

According to an embodiment of the present disclosure, a computer system for automatic selection of a computer-aided detection (CAD) algorithm including a database storing image data, a browser for navigating the data and selecting image data, an application receiving image data selected by the browser, and a selector selecting a CAD algorithm for processing the image data according to at least one of fixed attributes of the image data and an indication of a subject of the image data.

According to an embodiment of the present disclosure, a computer-implemented method for automatically selecting a computer-aided detection (CAD) processing algorithm includes analyzing an image header associated with image data, detecting image parameters of the image data, selecting, automatically, a CAD processing method for processing the image data based on the image header and image parameters, and processing the image data using the CAD processing method, wherein processed image data is one of output to a display device and stored as computer-readable code in a computer-readable media.

According to an embodiment of the present disclosure, a program storage device is provided, readable by machine, tangibly embodying a program of instructions executable by the machine to perform method steps for automatically selecting a computer-aided detection (CAD) processing algorithm. The method steps include analyzing an image header associated with image data, detecting image parameters of the image data, selecting, automatically, a CAD processing method for processing the image data based on the image header and image parameters, and processing the image data using the CAD processing method, wherein processed image data is one of output to a display device and stored as computer-readable code in a computer-readable media.

BRIEF DESCRIPTION OF THE DRAWINGS

Preferred embodiments of the present invention will be described below in more detail, with reference to the accompanying drawings.

DETAILED DESCRIPTION OF PREFERRED EMBODIMENTS

According to an embodiment of the present disclosure, a method for automatically selecting a CAD processing algorithm comprises analysis of a DICOM (Digital Imaging and Communications in Medicine) header, detection/segmentation and detection of orientation of body parts, detection of contrast, and manual input.

Analysis of the DICOM header may be used to find, for example, an area and volume covered by the volume, an imaging modality, acquisition parameters, reconstruction parameters, and body orientation. A DICOM file typically includes a header and a data set. The header may include a preamble and a prefix. The data set includes data elements. The preamble typically holds information specified by a user, including, for example, a patient's name, scan protocol details, etc.

Image processing techniques for detection/segmentation and detection of orientation of body parts may include, for example, detection and segmentation of the lungs and the colon.

Rules based on the information provided by these methods are processed to select an algorithm(s) for processing all or part of the images. For example, the pulmonary emboli computer detection algorithm will be selected if the modality is computed tomography (CT), the case has contrast and only those images containing the lungs will be processed. Further, portions of the images may be selected.

A classifier is trained to learn rules for algorithm selection. The classifier includes functionality to adapt continuously based on previous selections and feedback, for example, user feedback.

Specific information obtained during algorithm selection can be sent to the CAD algorithm to support the CAD algorithm processing.

The algorithm selection can be done on the images being processed by the CAD algorithm or on other images with the same coordinate system. For example, one can determine the location of the colon in the scout/topogram and use the location to select axial images to be used by the polyp detection algorithm or in a PET/CT volume the spine can be detected in the CT volume and the CAD algorithm applied to the corresponding part in the PET (positron emission tomography) volume.

In the figures various exemplary scenarios for using a detection system are illustrated. Further, numerals in parentheses indicate an exemplary sequence of actions.

Figure 1:
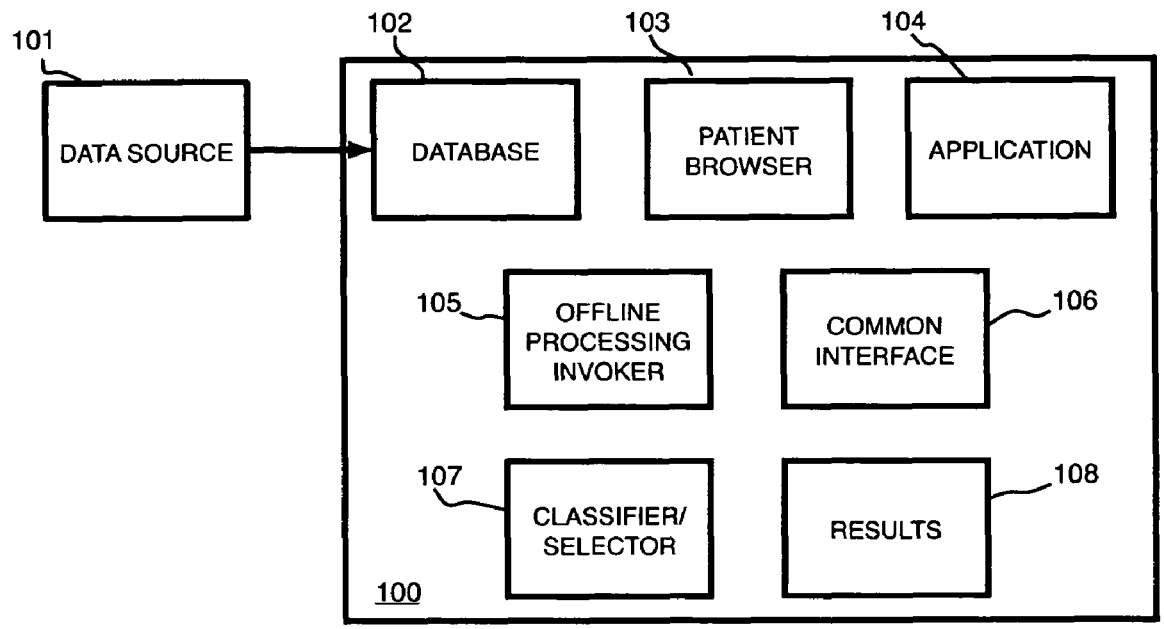
FIG. 1 is diagram of a system according to an embodiment of the present disclosure.

Referring to FIG. 1, a system implementing CAD algorithm selection 100 is coupled to a data source 101. The data source 101 may provide DICOM data or data according to another specification. The data source 101 may be, for example, an archive such as that stored on a compact disk (CD), a DICOM network, or shared database. The system 100 includes a database 102 receiving data from the data source 101, a patient browser 102 for reviewing data, and one or more applications 103 for processing/handling the data. The system 100 further includes an offline processing invoker 105, a common algorithm interface (CIF) 106, a classifier/selector 107 for selecting a data processing algorithm and a memory 108 for storing results. The results in this case may indicate which method was previously selected for a given set of DICOM parameters, image characteristics, e.g., contrast, orientation, etc., and an indication of the quality of the results. Components of the system 100 are interconnected via a network, such that, for example, data may be passed from one component to another, applications may access data, etc.

Figure 2:
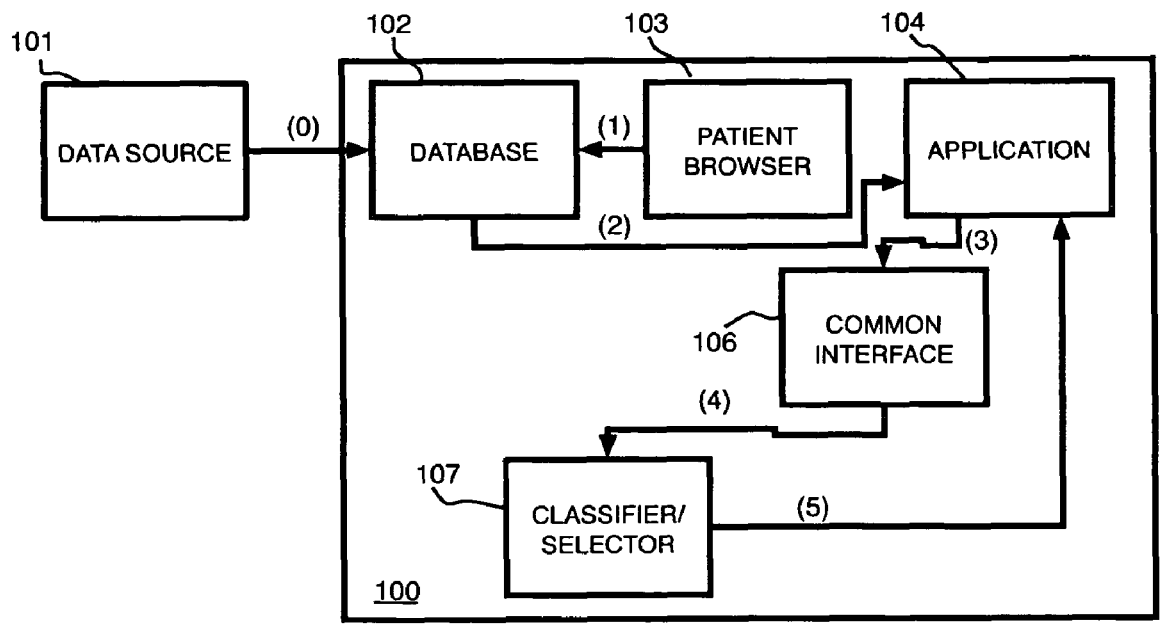
FIG. 2 is diagram of an online CAD system according to an embodiment of the present disclosure.

Referring to FIG. 2, in an online CAD system, such as a syngo® system, computation is done while a user is working with the system 100 to access a case. The CAD system 100 includes workflow features that start computation once a user has loaded a case where user interaction is not needed for processing. For example, the patient browser 103 is used to navigate the database 102. Selected portions of the database 102 are output to an application 104. The application 104 is augmented by the selector 107, wherein the application 104 and selector 107 are coupled via the CIF 106. The selector 107 passes results 108 back to the application 104.

The syngo system is a universal imaging platform including functionality for displaying and storing images, and having networking capabilities. The syngo system conforms to a consistent implementation and standards like DICOM for one modular set of applications across all diagnostic and therapeutic cycles.

Figure 3:
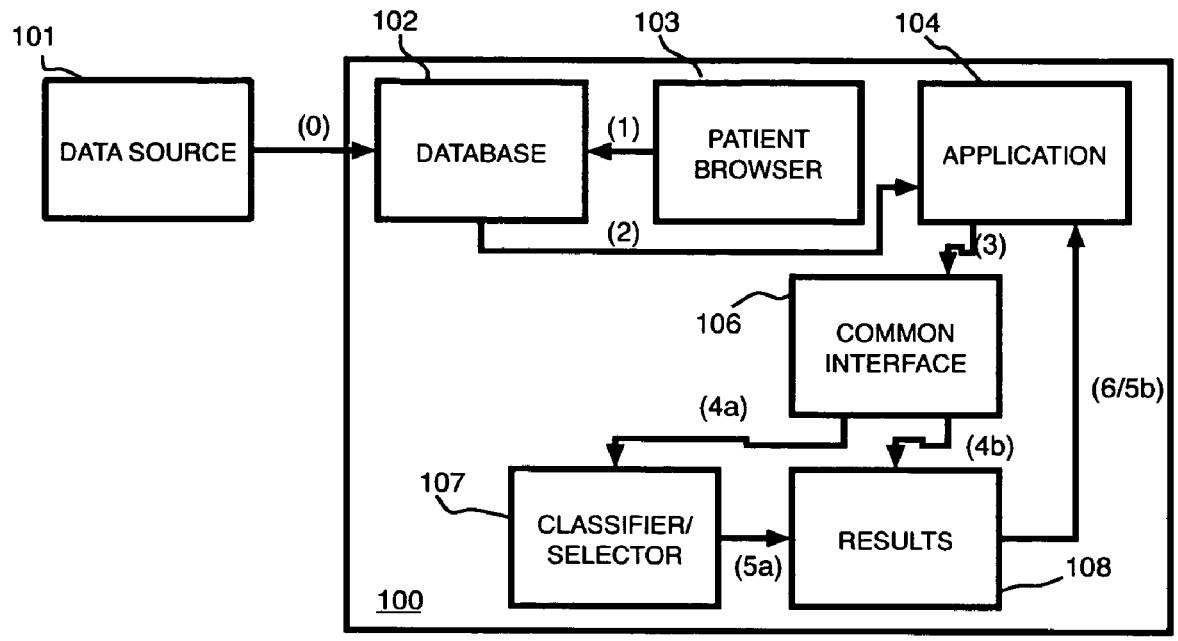
FIG. 3 is diagram of a bookmark mode CAD system according to an embodiment of the present disclosure.

Referring to FIG. 3, in a bookmark mode CAD system, the online CAD system is augmented by storing raw CAD results 108. If a case has been processed once and stored, e.g., see path 1-2-3-4a-5a-6, then subsequent case reads may be retrieved, e.g., path 1-2-3-4b-5b. Bookmark mode may be implemented by a single machine implementing an appropriate file system, or database. Bookmark mode can be implemented on different machines, where results are stored on an accessible database. Further, bookmark mode may be implemented via a patient browser 103, for example, wherein a set of patient records can be selected and browsed. The patient records may be stored in a file system, database 102, or the like.

Further, in the bookmark mode CAD system, wherein no previous results are available, the selector 107 is implemented. Where previous results are available, the CIF 106 is used to connect to the results 108.

Bookmark CAD results can be stored as, for example, database objects or file system entries.

Database objects may need more implementation/prototyping time. For a database, multiple database objects with the CAD results are easily handled. Database object names need to be meaningful. The objects can be archived and restored, integrated into PACS, etc. Objects may be deleted. The database can be implemented using the infrastructure for CADServermode. The database also allows for bookmark mode on syngo Navigator/Wizard and review on Leonardo.

An implementation of a file system supports multiple file system objects with the CAD results. The file system does not support archival and restoration functions innately. File system cleanup processes may be applied. A file system further supports demo-use cases. The results of an algorithm selection are stored with sufficient information to uniquely identify input patient data to the algorithm used in producing the results.

Figure 4:
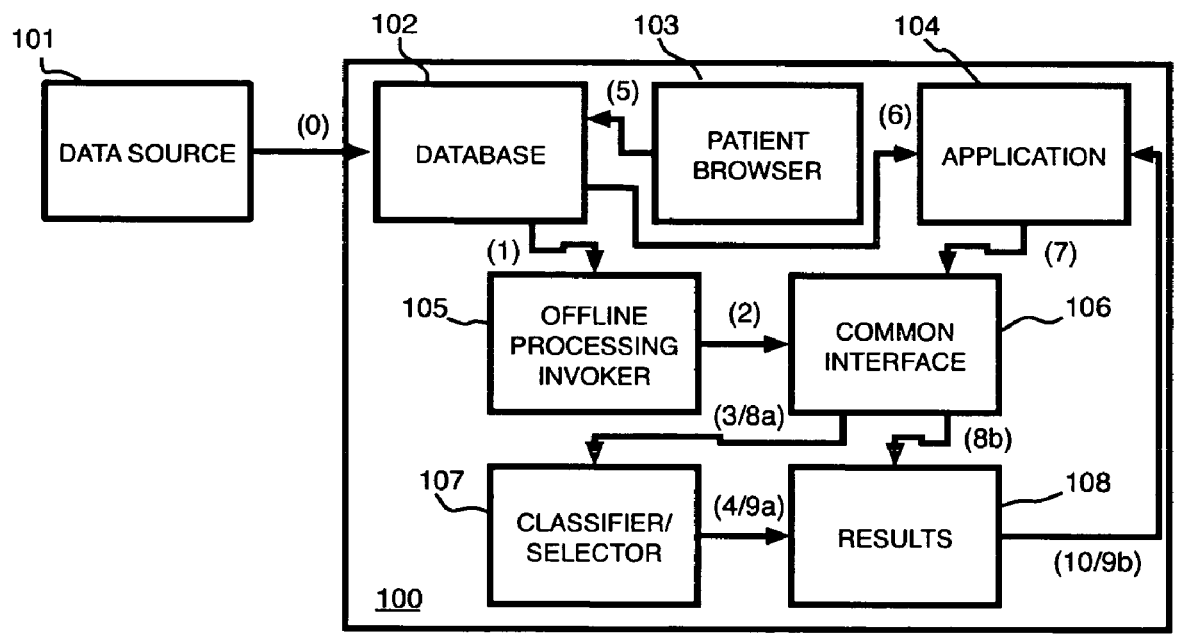
FIG. 4 is diagram of an offline CAD system according to an embodiment of the present disclosure.

Referring now to FIG. 4, in an offline CAD processing system, an offline CAD backend invoker 105 is implemented with stored raw CAD results 108. If a case has been processed once and stored, e.g., path 1-2-3/8a-4/9a-10, then subsequent case reads can be retrieved, e.g., path 5-6-7-8b-9b.

According to an embodiment of the present disclosure, a CAD server 101 receives input data that may be retrieved via the offline CAD invoker 105 for transmission of CAD results to a target/reading machine. In this case results can be retrieved by the target/reading machine without needed additional local resources (e.g., of the target/reading machine) such as CPU cycles and memory.

For offline CAD processing, an updated API between application and CIF blocks is needed, such that the CIF can know the patient information. The CIF may use an updated API. Results are stored, allowing for retrieval of results for repeated runs, for example, for demos at trade shows, or where a user runs implements the method first, which will take the execution time. When the user runs an application augmented by the memory having previous results, the wait time will be short.

The offline invoker may poll a database, listen to events for patient/study additions, or receive a command for manually selecting patient list. The offline invoker can output to the database or file system. Difference output formats can be supported, including, SR (Structured Reporting) and XML (extensible markup language).

System loading is a function of, for example, idle processing, executing functions such as for the automatic selection of a CAD processing method, and low priority processing.

Algorithm selection includes configurations to enter protocols for like body parts examined, etc. Fixed set of DICOM field(s) may be used as identification.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 5:
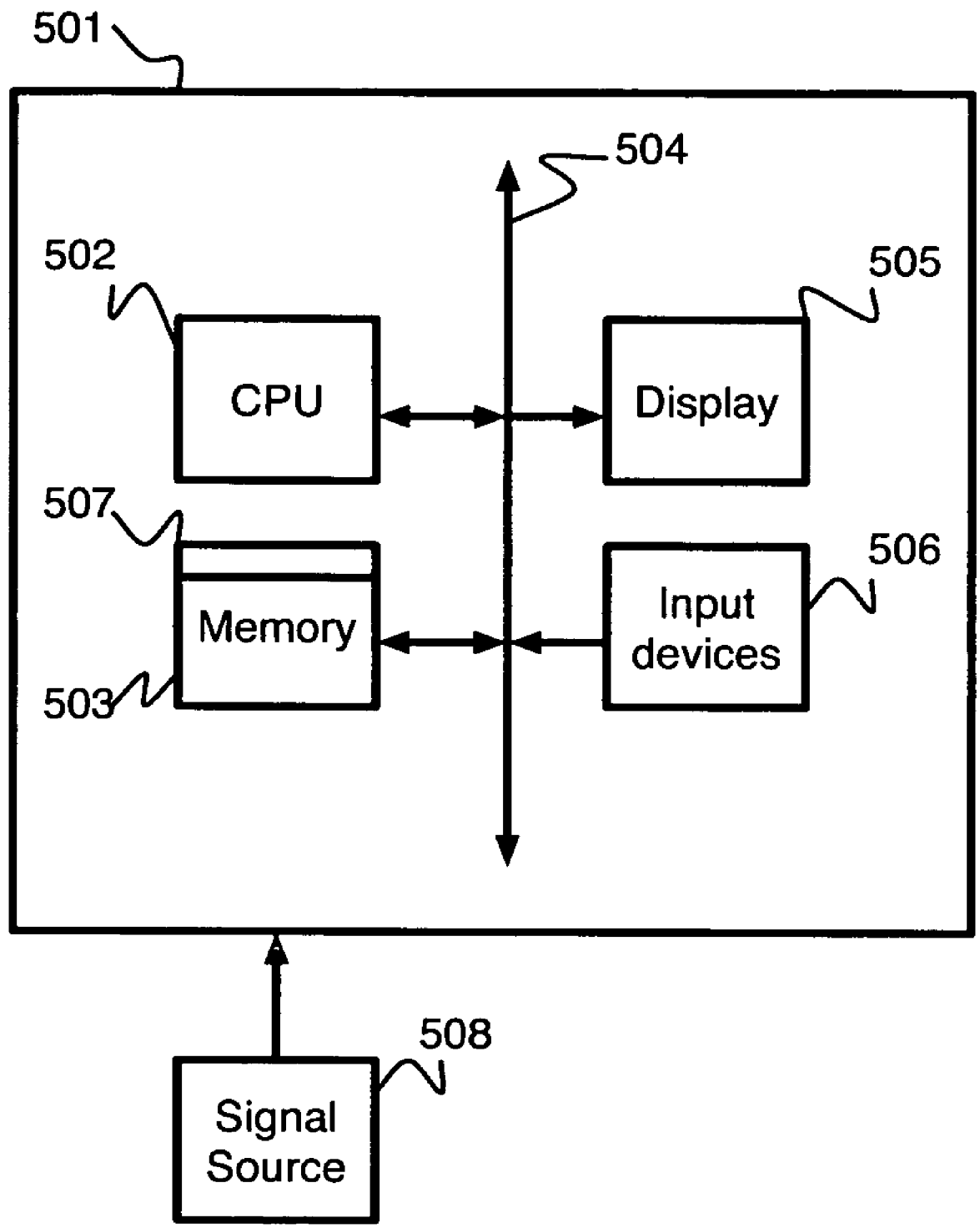
FIG. 5 is a diagram of a computer-system according to an embodiment of the present disclosure.

Referring to FIG. 5, according to an embodiment of the present disclosure, a computer system 501 for implementing a method for automatic selection of CAD algorithms can comprise, inter alia, a central processing unit (CPU) 502, a memory 503 and an input/output (I/O) interface 504. The computer system 501 is generally coupled through the I/O interface 504 to a display 505 and various input devices 506 such as a mouse and keyboard. The support circuits can include circuits such as cache, power supplies, clock circuits, and a communications bus. The memory 503 can include random access memory (RAM), read only memory (ROM), disk drive, tape drive, etc., or a combination thereof. The present invention can be implemented as a routine 507 that is stored in memory 503 and executed by the CPU 502 to process the signal from the signal source 508. As such, the computer system 501 is a general-purpose computer system that becomes a specific purpose computer system when executing the routine 507 of the present invention.

The computer platform 501 also includes an operating system and microinstruction code. The various processes and functions described herein may either be part of the microinstruction code or part of the application program (or a combination thereof), which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for a system and method for automatic selection of CAD algorithms, it is noted that modifications and variations can be made by persons skilled in the art in light of the above teachings. It is therefore to be understood that changes may be made in embodiments of the present disclosure that are within the scope and spirit thereof.

What is claimed is:

1. A computer system for automatic selection of a computer-aided detection (CAD) algorithm comprising:
    a database storing image data;
    a browser for navigating the data and selecting image data;
    an application receiving image data selected by the browser; and
    a selector selecting a CAD algorithm for processing the image data according to at least one of fixed attributes of the image data and an indication of a subject of the image data wherein the fixed attributes are coded in a header of an image file corresponding to the image data and the image header is analyzed by determining an area of the image data, an imaging modality used to capture the image data, and acquisition parameters used to capture the image data.

2. The computer system of claim 1, further comprising a common interface algorithm for connecting the application and the selector.

3. The computer system of claim 1, further comprising a memory storing results, the memory operatively associated with a common interface, the selector, and the application.

4. The computer system of claim 1, further comprising a processor executing instructions of the browser, the application and the selector.

5. A computer-implemented method for automatically selecting a computer-aided detection (CAD) processing algorithm comprising:
    analyzing an image header associated with image data wherein analyzing the image header comprises determining an area of the image data, an imaging modality used to capture the image data, and acquisition parameters used to capture the image data;
    detecting image parameters of the image data;
    selecting, automatically, a CAD processing method for processing the image data based on the image header and image parameters; and
    processing the image data using the CAD processing method, wherein processed image data is one of output to a display device and stored as computer-readable code in a computer-readable media.

6. The computer-implemented method of claim 5, wherein analyzing the image header comprises determining reconstruction parameters used in generating the image data, and a body orientation of a subject of the image data.

7. The computer-implemented method of claim 5, wherein the image parameters include orientation of a subject of the image data and contrast of the image data.

8. The computer-implemented method of claim 5, wherein the selecting the CAD processing method is further based on previous selections.

9. The computer-implemented method of claim 5, further comprising forwarding information obtained during selection of the CAD processing method to a CAD algorithm to support the processing.

10. A program storage device readable by machine, tangibly embodying a program of instructions executable by the machine to perform method steps for automatically selecting a computer-aided detection (CAD) processing algorithm, the method steps comprising:
    analyzing an image header associated with image data wherein analyzing the image header comprises determining an area of the image data, an imaging modality used to capture the image data, and acquisition parameters used to capture the image data;
    detecting image parameters of the image data;
    selecting, automatically, a CAD processing method for processing the image data based on the image header and image parameters; and
    processing the image data using the CAD processing method, wherein processed image data is one of output to a display device and stored as computer-readable code in a computer-readable media.

11. The method of claim 10, wherein analyzing the image header comprises determining reconstruction parameters used in generating the image data, and a body orientation of a subject of the image data.

12. The method of claim 10, wherein the image parameters include orientation of a subject of the image data and contrast of the image data.

13. The method of claim 10, wherein the selecting the CAD processing method is further based on previous selections.

14. The method of claim 10, further comprising forwarding information obtained during selection of the CAD processing method to a CAD algorithm to support the processing.

* * * * *